Figure 1:
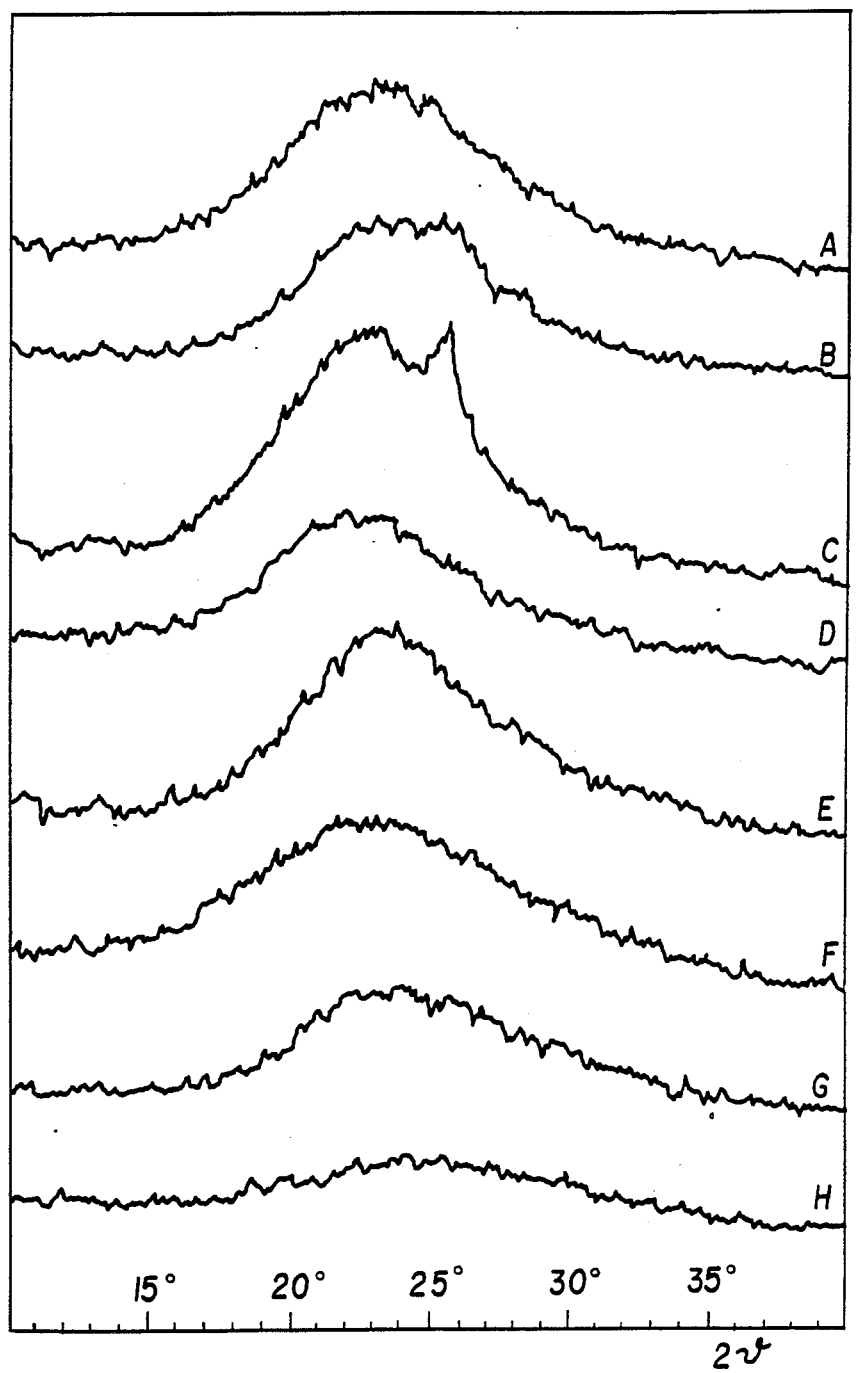

United States Patent [19]

Padovan et al.

[11] Patent Number: 4,968,842

[45] Date of Patent: Nov. 6, 1990

[54] CATALYTIC PROCESS FOR THE MANUFACTURE OF OXIMES

[75] Inventors: Mario Padovan, Milan; Fausto Genoni, Samarate; Giuseppe Leofanti, Canegrate; Guido Petrini, Galliate; Paolo Roffia, Saronno; Alberto Cesana, Carate Brianza, all of Italy

[73] Assignee: Montedipe, S.p.A., Milan, Italy

[21] Appl. No.: 407,733

[22] Filed: Sep. 15, 1989

Related U.S. Application Data

[62] Division of Ser. No. 369,077, Jun. 20, 1989.

[30] Foreign Application Priority Data

Jun. 23, 1988 [IT] Italy .................. 21076 A/88

[51] Int. Cl.$^5$ ........................... C07C 249/04
[52] U.S. Cl. .................. 564/253; 564/265; 564/267; 564/268; 564/266
[58] Field of Search ............... 504/253, 265, 267, 266, 504/268

[56] References Cited

U.S. PATENT DOCUMENTS 4,504,681  3/1985  Armor .................. 564/253
4,560,797 12/1985  Yamanis et al. .......... 564/253
4,794,198 12/1988  Roffia et al. ........... 564/253

FOREIGN PATENT DOCUMENTS 208311  1/1987  European Pat. Off. ........ 564/253

*Primary Examiner*—James H. Reamer
*Attorney, Agent, or Firm*—Morgan & Finnegan

[57] ABSTRACT

The invention concerns a catalytic process for the manufacture of oximes by ammoximation of the corresponding carbonyl compounds, characterized in that the catalyst is a solid composition consisting of silicon, titanium and oxygen, chemically combined with each other, and in that the titanium amount, expressed as $TiO_2$, ranges from 1 to 95% by weight, the XR diffractogam of said composition being a smooth-trend line (halo), typical of the amorphous solids.

18 Claims, 3 Drawing Sheets

CATALYTIC PROCESS FOR THE MANUFACTURE OF OXIMES

This is a division of application Ser. No. 369,077, filed June 20, 1989.

BACKGROUND OF THE INVENTION

European patent No. 208,311 teaches how to obtain cyclohexanone-oxime in the liquid phase from cyclohexanone, ammonia and hydrogen peroxide. In the presence of a catalyst consisting of a crystalline compound having a zeolitic structure; this structure, however, requires a treatment of the silicon compounds and of the titanium compounds with proper organic compounds, which are known as templating agents (in particular tetraalkyl-ammonium hydroxides or salts thereof) and which can be synthesized only with extreme difficulty; sometimes the silicon and/or titanium source consisted of an amorphous solid material (See European patent No. 299,430 and European patent application No. 88/116,870), but the treatment with templating agents was nevertheless assumed to be unavoidable for obtaining a catalytically active structure. The preparation of said crystalline structure required a very long operative (residence) time and the use of high temperatures and pressures; furthermore, it was necessary to submit the catalyst to complex post-treatments.

The Applicant has now found that the synthesis of the oximes (starting from carbonyl compounds, $H_2O_2$ and $NH_3$) can be promoted also by catalysts, based on titanium and silicon, which do not exhibit said zeolitic structure and which can be prepared without any use of templating agents in a very short time.

DISCLOSURE OF THE INVENTION

In its widest form, the invention concerns a catalytic process for the manufacture of oximes by reacting in the liquid phase the corresponding carbonyl compounds with ammonia and hydrogen peroxide (ammoximation), the catalyst being selected from the solid compositions consisting at least of silicon, titanium and oxygen, chemically combined with each other, said compositions being characterized by a XR diffractogram, obtained by utilizing the $K\alpha$ radiation of copper in the ($2\theta$) range from 10° to 40°, in which the peaks, which are typical of the crystalline solids, are replaced by a smooth-trend line (halo), typical of the amorphous solids, an example being represented by diffractograms A, B, D, E, F, G and H in FIG. 1. Said compositions are furthermore characterized, optionally also by those XR diffractograms which exhibit, besides said halo, the typical reflexes of anatase and/or of rutile and/or of brookite; an example is represented by diffractogram C on FIG. 1. The infrared spectrum of said compositions (obtained through infrared spectrophotometry in the range from 400 to 1300 $cm^{-1}$), has an intermediate trend between the trend of the amorphous silica spectra and the trend of the titanium oxide spectrum, which are known from the prior art; reference should be made in this connection to: "Infrared Analysis of Polymers, Resins and Additives; An Atlas"; (Volume 2; Carl Hauser VERLAG Muenchen (1973); spectrum 2317 for silica; spectra 2353 and 2354 for titanium dioxide). An example of the infrared spectra of said compositions are spectra A, B, C, D, E, F, G and H on FIG. 2. Depending on the selected titanium source, on the catalyst preparation method and on the amount of titanium, other bands, alien to amorphous silicas and to titanium-silicalites, for instance the band at 750 $cm^{-1}$ described in example 4, may optionally appear in said infrared spectrum.

Some of these compositions are known from the literature as binary oxides or mixed oxides; see for example "Advances in Catalysis; Vol. 27 (1978), pages 136-138 (Academic Press Publisher). The absence, in the XR diffractogram, of the reflexes typical of titanium-silicalite, the peak diffractogram of which is reported by the Journal of Catalysis [Volume 61 (1980). Pages 390-396] and the absence from the infrared spectrum of the absorption band at about 550 $cm^{-1}$, bound—as it is known—to the structural vibrations of the zeolitic structures of the PENTASIL type, as it is described for instance by Breck [ZEOLITES; volume 4 (1984), pages 369-372], proves the absence of zeolite-structure-showing crystalline phases typical of the titanium-silicalite, including the phases consisting of crystallites having a size below the X-ray resolution (resolving) power.

The titanium amount in said compositions (expressed as $TiO_2$) ranges from 1 to 95% and preferably from 4.5 to 50% by weight. The surface area of said compositions is preferably from 10 to 800 and, even better, from 200 to 800 $m^2/g$; the pore volume of the same compositions ranges from 0.1 to 2.5 $cm^3/g$ and the average diameter of the pores is greater than 0.70 nm and preferably ranges from 1 to 40 nm.

The new catalysts have been used also in continuous operations, for many tens of hours, without any sign of exhaustion, with yields equal to and sometimes higher than the ones of the discontinuous tests, and they have proved to be very active not only in the case of the ammoximation of aldehydes and ketones, but also in the case of other organic syntheses, such as e.g. the synthesis of N,N-dialkyl-hydroxylamines, which is described in European patent application 88/117,950.

Aldehydes which can be catalytically converted into oxime are generally the aldehydes of formula $R_1CHO$, where $R_1$ is selected from alkyl, cycloalkyl, aryl or heterocyclic groups (containing O, N or S in the ring), having 1 to 20 carbon atoms. Alkyl group means also an arylalkyl group, a cycloalkyl-alkyl group or an alkyl group substituted with heterocyclic groups; aryl group means also an alkyl-aryl group, cycloalkyl-aryl group or an aryl group substituted with heterocyclic groups; cycloalkyl group means also an alkyl-cycloalkyl group, an aryl-cycloalkyl group or a cycloalkyl group substituted with heterocyclic groups; heterocyclic group means also an alkyl-, cycloalkyl- or aryl-heterocyclic group.

Ketones which can be catalytically converted into oxime are generally the ketones of formula $R_2$—CO—$R_3$, where $R_2$ and $R_3$, equal to or different from each other, have the same meaning as $R_1$ and can be linked at their end, thus forming a carbocyclic or heterocyclic ring. Excellent results were obtained in the ammoximation of acetone, cyclohexanone, methylethyl-ketone(butan-2-one), acetophenone, benzophenone, terbutyl-cyclohexanone, cyclo-dodecanone, enanthic aldehyde (1-heptanal) and benzaldehyde.

The catalyst can be prepared starting from various titanium and silicon sources, according to methods which are known for the preparation of heterogeneous catalysts; as compared with the crystalline compounds showing zeolitic-structure, the catalyst of the invention can be prepared by means of a very simplified method and the influence of the catalyst cost on the oxime synthesis process is remarkably reduced.

Without limiting at all the scope of the invention, a few alternatives are cited hereinbelow.

The catalyst of the invention can be prepared by hydrolysis of alcoholic solutions containing silicon and titanium alcoholates; see for example the Journal of Non-crystalline Solids, 82 (1986), pages 97–102.

As an alternative, the catalyst can be obtained from aqueous solutions of soluble compounds of silicon and of titanium, by means of co-precipitation with a base (for example ammonium hydroxide); see for example the Journal of Catalysis, 35 (1974); pages 225–231; and still the same Journal of Catalysis, 105 (1987), pages 511–520.

According to another alternative, a commercial amorphous silica showing a great surface area (for example a microspheroidal product) and a high pore volume can be impregnated with aqueous solutions or non-aqueous solutions of soluble titanium compounds, resorting for example, to the incipient wetness technology; see e.g. Applied Catalysis, 32 (1987), pages 315–326; and Langmuir 3 (1987), pages 563–567.

According to a still further alternative, a volatile titanium compound can be adsorbed as a vapour by a commercial amorphous silica having a high surface area and a high pore volume; see for example Applied Catalysis, 23 (1986), pages 139–155.

After its preparation, the catalyst can be directly utilized for the ammoximation, or it can be calcined in a stream of air, or of another gas or under vacuum, at temperatures from 50° to 800° C. As a soluble source of titanium, the following ones can be cited, merely as an example:

alkyl-titanates and in particular tetraisopropyl-titanate and di-isopropyl-bis(triethanolamine)-titanate;

tanium halides and in particular titanium tetrachloride ($TiCl_4$) and titanium trichloride ($TiCl_3$);

complex titanates and in particular ammonium hexafluorotitanate ($(NH_4)_2TiF_6$);

combinations and equivalents thereof.

The conversion of ketones (or of aldehydes) into oxime must be generally carried out in the liquid phase at a temperature from 25° to 100° C., preferably from 40° to 90° C. (even better from 60° to 90° C.); tests carried out at 15° C. supplied quite unsatisfactory results. The reaction can be generally conducted at atmospheric pressure or at pressures slightly higher than the atmospheric pressure, in order to maintain dissolved, in the reaction medium, at least an ammonia amount corresponding to the synthesis requirement. The catalyst can be arranged on a fixed bed (in particular a trickle bed) or finely dispersed in the reaction medium, provided the reactors have a wall compatible with hydrogen peroxide. If the reaction is performed discontinuously, it is advisable to use 0.1 to 50 parts by weight (preferably 1 to 20 parts) of catalyst for 100 parts of ketone or of aldehyde; if the reaction is performed incontinuous, a space velocity from 0.1 to 200 kg/hour of ketone or of aldehyde per kg of catalyst is advisable. The $H_2O_2$/ketone (or aldehyde) molar ratio must generally range from 0.3 to 2.5 and preferably from 0.5 to 1.3, where $H_2O_2$ means hydrogen peroxide at a 100% purity degree (dilution water being therefore excluded). The $NH_3/H_2O_2$ molar ratio must be equal to or higher than 1 (preferably 1.5), otherwise disturbing parallel reactions would take place. The reaction medium may consist of water or of an organic solvent; exceptional results were obtained by the use, as a solvent, of t-butyl alcohol and/or cyclohexanol, optionally in admixture with dioxane or toluene. The tert:butanol (and/or cyclohexanol)/ketone (or aldehyde) molar ratio shall generally range from 0.1 to 100. At the end of the reaction, the oxime can be separated in different ways, for instance by means of an extraction with proper solvents such as benzene, toluene, or the same ketone (or aldehyde) utilized for the synthesis, whereby a hydrophobic organic phase and an aqueous phase are formed. Oxime and unreacted ketone (or aldehyde) flow into the organic layer; the aqueous layer, containing the $NH_3$ excess as well as traces of ketone (or aldehyde) and of oxime, can be usefully recycled to the reaction area. As an alternative, the extraction may be conducted simultaneously with the synthesis, by operating in a two-phase system; this system can be profitably prepared by using a couple of solvents having different characteristics, for example tert.butanol (hydrophilic) and toluene (hydrophobic). When ammoximation is conducted in continuous, it is suggested to maintain the space velocity from 0.1 to 200 kg/h of ketone or of aldehyde (preferably from 2 to 200 kg/h) per kg of pure catalyst (binders excluded) and to feed the ketone or the aldehyde in admixture with the organic solvent, for instance tert.butanol (and/or cyclohexanol); in the ammoximation reactor it is advantageous to use the trickle-bed technology. One of the alternatives is the continuous reaction in a suspended bed, under stirring; in this case it is advisable to feed the reactants through dipping pipes submersed beneath the liquid level.

The following examples are supplied in order to illustrate the invention; however they are by no way to be construed as to be a limitation of the scope thereof.

EXAMPLE 1

30 g of a microspheroidal silica, as it is usually available, having a surface area of 408 m²/g, a pore volume equal to 2 cm³/g and an average particle diameter equal to 0.105 mm, were impregnated, according to the incipient wetness technology, with 65 cm³ of an aqueous solution, containing 45% by weight of di(isopropyl)-bis(triethanolamine)-titanate of formula: $(C_3H_7O)_2$-$Ti(C_6H_{14}NO_3)_2$, marketed by Dynamit Nobel under the trade-name TEAT. After a 4-hour rest in the air, the impregnated silica was dried in an oven at 80° C. and then calcined in the air at 500° C. for 6 hours. The thus obtained catalyst contained 12.3% by weight of titanium, expressed as $TiO_2$. The corresponding X-ray diffractogram is marked with the letter A on FIG. 1. In the infrared spectrum of the catalyst prepared according to this example (spectrum A in FIG. 2), an absorption band with a maximum substantially at 960 cm$^{-1}$ appears. A band very near to said band of spectrum A is indicated by U.S. Pat. No. 4,410,501 to be typical of titanium silicalites and as a proof of the presence of titanium in the zeolitic structure of silicalite, because this band does not appear in the infrared spectrum of pure silicalite, nor in the infrared spectrum of titanium oxides. However, that is not quite exact; in the present case, the presence of a band with a peak at about 960 cm$^{-1}$ is not sufficient, alone, to prove the presence of structural Ti. The same band appears in fact also in the infrared spectrum of the amorphous silica, utilized by the Applicant for preparing the catalyst, while for a complete identification of titanium silicalite also a second typical band, with a peak at about 550 cm$^{-1}$, is necessary, said band being missing in the new catalysts of the present invention.

EXAMPLE 2

Into a glass reactor, equipped with a stirrer and a heating jacket, beforehand blanketed with an inert gas (nitrogen) there were introduced 7.5 g of the catalyst powder obtained according to example 1; 21 g of water (1.17 moles), 25 g of t.-butyl alcohol (0.34 moles) and 4 g of ammonia (0.24 moles) were then added. The whole was stirred and 10.34 g of cyclohexanone (0.105 moles) were charged, thus forming a two-phase (solid-liquid) system, which was maintained homogeneous by intense stirring. The temperature was raised up to 80° C. by conveying a thermostatic liquid into the reactor jacket. Then, by means of a metering pump, an aqueous solution of hydrogen peroxide, at 33% by weight, began to be fed to the reactor. During heating, the pressure slightly rose above the atmospheric pressure. $H_2O_2$ was added in 5 hours and an overall amount of 11.33 g of $H_2O_2$ (0.096 moles) was fed in; during the addition, the pressure inside the autoclave decreased. The resulting suspension was additioned, after cooling, with ethyl ether and was stirred for a few minutes; the aqueous phase and the ethereal phase were then separated from the catalyst by means of filtration. The liquid phases were separated in a separatory funnel, and the gas-chromatographic analysis revealed a cyclohexanone conversion equal to 97.6% and a selectivity to oxime equal to 97.5%; the oxime yield (with respect to $H_2O_2$) was equal to 88.2%. Data and results are recorded on Table 1.

EXAMPLE 3

30 g of the amorphous silica of example 1 were impregnated with 60 $cm^3$ of a 6M aqueous solution of HCl containing 6.2 g of $TiCl_4$; after a 4-hour rest in the air, the impregnated silica was dried in an oven at 120° C. for 16 hours and calcined in the air at 200° C. for 6 hours. The resulting catalyst contained 8.1% by weight of titanium, expressed as $TiO_2$. The corresponding XR diffractogram is indicated by the letter B on FIG. 1; it does not appreciably differ from diffractogram A of example 1. The corresponding infrared spectrum is marked with letter B on FIG. 2 and does not exhibit appreciable differences from spectrum A of example 1.

EXAMPLE 4

8 g of $TiO^2$ were dissolved at 80° C. in 30 $cm^3$ of an aqueous solution of HF at 50% by weight in a platinum dish. To the thus obtained limpid solution, 100 $cm^3$ of a solution at 17% by weight of $NH_4F$ were added. It was slowly evaporated and drying was carried out at 100° C. during 16 hours. The resulting product was corresponding to ammonium hexafluorotitanate $(NH_4)_2TiF_6$; 30 g of the amorphous silica of example 1 were impregnated (according to the incipient wetness technique) with 60 $cm^3$ of an aqueous solution of $(NH_4)_2TiF_6$ at 5.6% by weight. After impregnation, the silica was allowed to rest during 4 hours at room temperature and then it was calcined at 300° C. for 2 h in the air. The thus obtained catalyst contained 4.6% by weight of titanium, expressed as $TiO_2$. The corresponding XR diffractogram is reported in FIG. 1 and is indicated by letter C; it shows the presence of the more intense reflex of anatase (d=0.352 nm; $2\theta=25.3°$); see card JCPDS—21—1272. The corresponding infrared spectrum is marked with letter C in FIG. 2; all the bands of spectrum A of example 1 appear therein. Apparent is also a band with the peak at about 750 $cm^{-1}$, which is due to the use of the particular titanium source (ammonium hexafluorotitanate) in the preparation of the catalyst. This statement is proved by the results of a blank test (in the absence of of titanium) carried out beforehand; the same amophours silica of example 1 had been impregnated (by means of the incipient wetness technique) with an aqueous solution of ammonium fluoride ($NH_4F$) free from titanium; after a 4-hour rest at room temperature and a calcination in the air at 300° C. for 24 hours, the product was characterized by a spectrum in which, in the absence of titanium, said band at 750 $cm^{-1}$ was clearly apparent (see FIG. 3).

EXAMPLE 5

50 g of an amorphous microspheroidal silica having a surface area of 408 $m^2/g$ and a pore volume equal to 2.10 $cm^3/g$ were calcined at 300° C. for 1 hour and subsequently impregnated with 115 $cm^3$ of a solution consisting of 35 $cm^3$ of tetraisopropyl-orthotitanate and of 80 $cm^3$ of isopropyl alcohol, which had been previously dehydrated on a molecular sieve (zeolite 4A). The so impregnated silica was allowed to rest during 4 hours at room temperature; then it was dried at 120° C. for 16 hours. The resulting catalyst contained 16.4% by weight of titanium, expressed as $TiO_2$. The corresponding XR diffractogram is indicated by letter D in FIG. 1 and does not appreciably differ from diffractogram A of example 1. The corresponding infrared spectrum is shown in FIG. 1 and is indicated by letter D; it does not exhibit appreciable differences from spectrum A of example 1.

EXAMPLE 6

Figure 2:
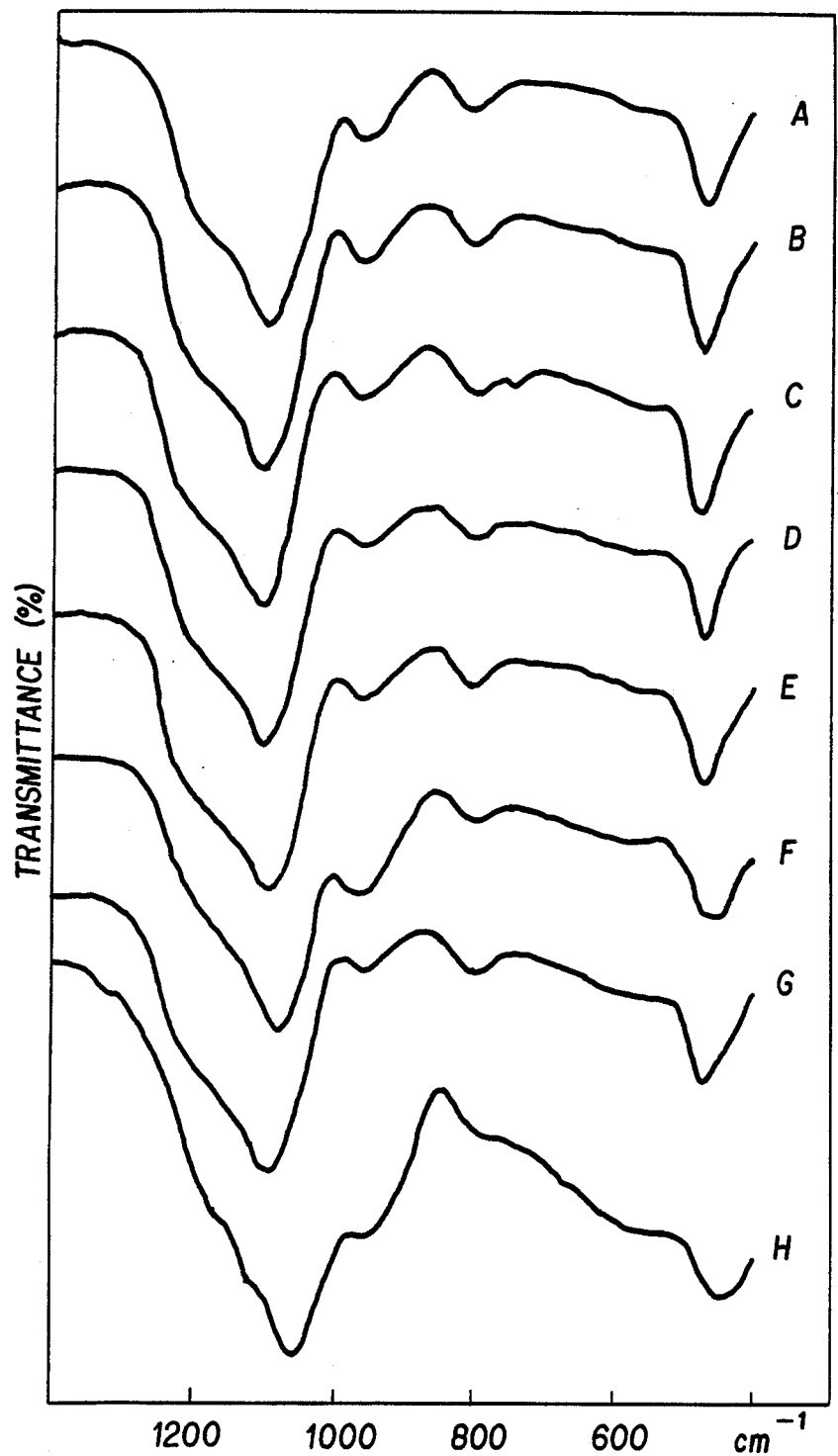
Figure 3:
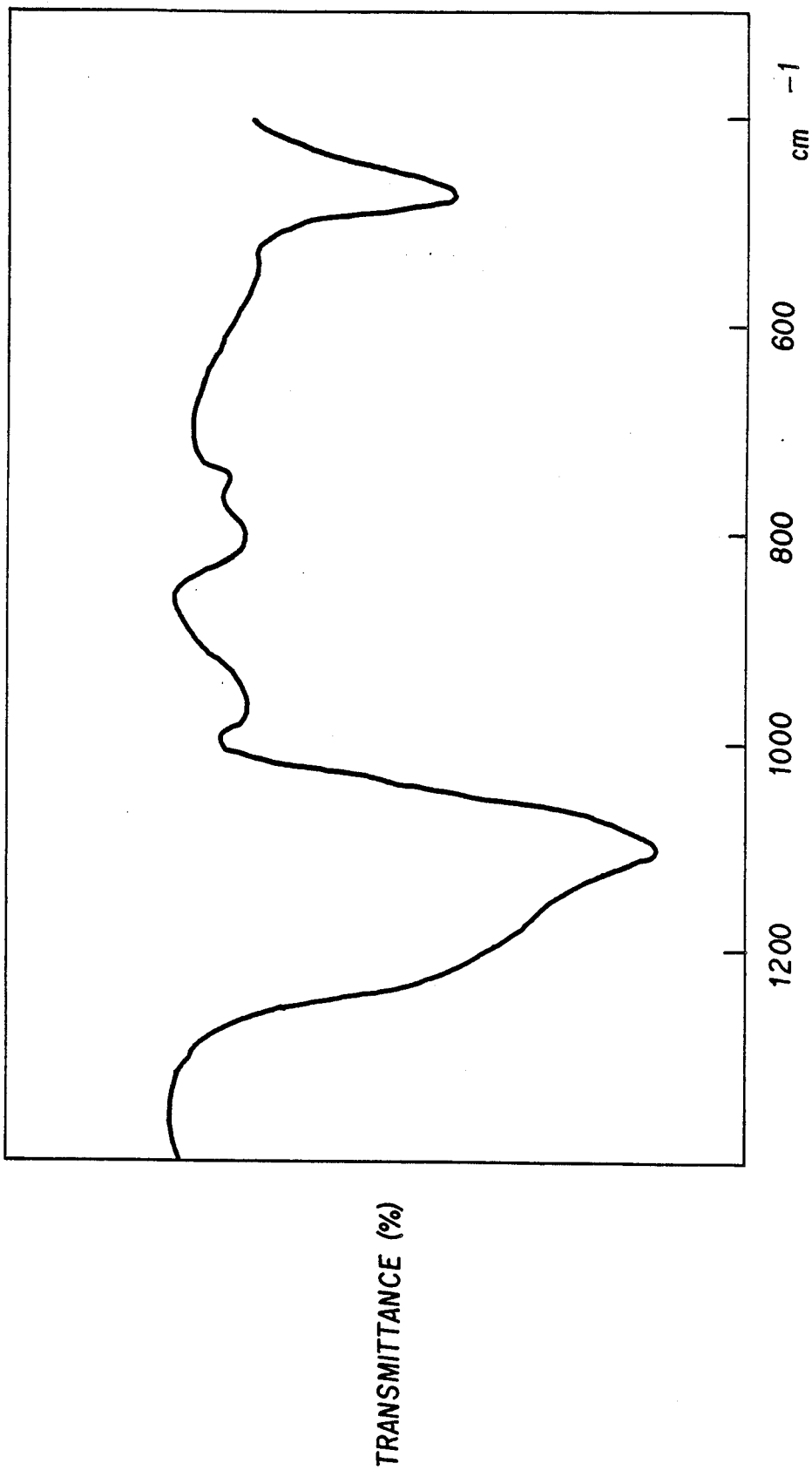

Example 5 was repeated, the drying being followed by a calcination in the air at 300° C. for 2 hours. The resulting catalyst contained 16.4% by weight of titanium expressed as $TiO_2$. The corresponding XR diffractogram is marked with letter E in FIG. 1 and does not significantly differ from diffractogram A of example 1. The corresponding infrared spectrum is shown in FIG. 2 and is indicated by letter E; it does not exhibit significant differences as compared with spectrum A of example 1.

EXAMPLE 7

Into a 500 $cm^3$ flask, maintained in an inert gas atmopshere ($N_2$), 100 g of tetraethyl-orthosilicate and 21 g of tetraisopropyl-orthotitanate were charged. To the limpid solution of the two alcoholates, 100 $cm^3$ of deionized water were added under stirring and by means of a slow dropping (5 $cm^3$/minute). At the end, the resulting gel was left under stirring during four hours. Filtration, drying at 120° C. for 16 hours and calcination at 300° C. in the air for 2 hours were carried out. The resulting catalyst contained 18.2% by weight of titanium expressed as $TiO_2$. The corresponding XR diffractoram is marked with letter F in FIG. 1; it exhibits no reflex which could be considered as an index of the presence of crystalline phases. The corresponding infrared spectrum is reported in FIG. 2 and is indicated by letter F; all the bands which are present in spectrum A of example 1 appear therein. The position of the peak of some bands (in particular of the most intense band with the peak at about 1100 $cm^{-1}$) appears slightly shifted towards lower values of the wave number. Such phenomenon is typical of the compositions containing Ti, Si and O which are obtained by co-precipitation from soluble compounds of titanium and silicon. In this connection, reference should be made, for example, to the article by L. G. Karakchiev in KINETIKA I KATALIZ., vol. 6, No. 5 (September-October 1965) pages 904–908.

EXAMPLES 10 TO 16

Example 2 was repeated, the catalyst of example 2 being replaced by the catalysts prepared according to examples 3 to 9; the results are reported in Table 1.

TABLE 1

| EXAMPLE | 2 | 10 | 11 | 12 | 13 | 14 | 15 | 16 |
|---|---|---|---|---|---|---|---|---|
| Catalyst | from ex. 1 | from ex. 3 | from ex. 4 | from ex. 5 | from ex. 6 | from ex. 7 | from ex. 8 | from ex. 9 |
| $TiO_2$ (%) | 12.3 | 8.1 | 4.6 | 16.4 | 16.4 | 18.2 | 26.0 | 38.2 |
| Pore volume (cm3/g) | 0.8 | 1.5 | 0.8 | 1.9 | 1.9 | 0.66 | 1.0 | 0.23 |
| Surface area (m2/g) | 345 | 354 | 231 | 364 | 389 | 318 | 499 | 422 |
| Average diam. of pores (nm) | 9 | 17 | 14 | 21 | 20 | 8 | 8 | 2 |
| XR diffract. | A | B | C | D | E | F | G | H |
| I.R. spectrum | A | B | C | D | E | F | G | H |
| Ketone conversion (%) | 97.6 | 91.9 | 64.2 | 95.7 | 99.5 | 98.8 | 99.3 | 96.0 |
| Ketone selectivity to oxime (%) | 97.5 | 94.2 | 100.0 | 98.7 | 97.4 | 97.0 | 93.7 | 94.8 |
| Oxime yield (on $H_2O_2$) (%) | 88.2 | 82.0 | 64.6 | 89.2 | 90.0 | 87.1 | 87.4 | 88.0 |

EXAMPLE 8

50 g of an amorphous silica, marketed by GRACE under the trade-name GRADE 360, having a surface area equal to 600 m²/g and a pore volume equal to 1.1 cm³/g, were calcined at 300° C. for 2 hours and were subsequently impregnated with 70 cm³ of tetraisopropyl-orthotitanate. The silica, so impregnated, was allowed to rest during 4 hours at room temperature; then it was dried at 120° C. for 16 hours and calcined at 300° C. in the air during 2 hours. The resulting catalyst contained 26.0% by weight of titanium expressed as $TiO_2$. The corresponding XR diffractogram is marked with letter G in FIG. 1. The corresponding infrared spectrum is shown in FIG. 2 and is indicated by letter G; it does not exhibit appreciable differences from spectrum A of example 1.

EXAMPLE 9

To a solution of 75 g of tetraisopropyl-orthotitanate and 75 g of tetraethyl-orthosilicate in 150 cm³ of anhydrous isopropyl alcohol there were added, under stirring and at room temperature, 150 cm³ of $H_2O$. Stirring was carried on four 4 hours, then the product was filtered and the resulting solid was dried at 120° C. during 16 hours. The catalyst, so obtained, contained 38.2% by weight of titanium, expressed as $TiO_2$; the corresponding XR diffractogram is marked with letter H in FIG. 1. The corresponding infrared spectrum is reported in FIG. 2 and is indicated by letter H; all the bands present in spectrum A of example 1 appear therein. The position of the peak of such bands is shifted towards lower values of the wave number, analogously with what had been observed in connection with example 7; furthermore, in the range from 400 to about 800 cm⁻¹, the spectrum shape is appreciably modified as compared with the one typical of the amorphous silica due to the emerging of the wide absorption band of titanium oxide, as it is known from the literature. In this connection, reference should be made, for example, to the article by L. G. Karakchiev in KINETIKA I KATALIZ., vol. 6, No. 5 (September-October 1965), pages 904–908.

What we claim is:

1. A catalytic process for the manufacture of oximes, consisting essentially of reacting in the liquid phase the corresponding carbonyl compounds with ammonia and hydrogen peroxide, characterized in that the catalyst is a solid composition consisting at least of silicon, titanium and oxygen, chemically combined with each other, wherein the titanium amount, expressed as $TiO_2$, ranges from 1 to 95% by weight, on the whole composition, and wherein the XR diffractogram of said composition (obtained by means of the $K\alpha$ radiation of copper) is showing, in the ($2\theta$) range from 10° to 40°, a smooth-trend line (halo), which is typical of the amorphous solids.

2. A catalytic process for the manufacture of oximes, consisting essentially of reacting in the liquid phase the corresponding carbonyl compounds with ammonia and hydrogen peroxide, characterized in that the catalyst is a solid composition consisting at least of silicon, titanium and oxygen, chemically combined with each other, wherein the titanium amount, expressed as $TiO_2$, ranges from 1 to 95% by weight, on the whole composition, and wherein in the XR diffractogram (obtained by means of $K\alpha$ radiation of copper) of said composition, in the range ($2\theta$) from 10° to 40°, the reflexes typical of the crystalline solids are replaced by a smooth-trend line (halo), which is typical of the amorphous solids.

3. The process of claim 1 or 2, wherein said XR diffractogram also the reflexes typical of anatase and/or of rutile and/or of brookite appear.

4. The process according to claim 1, wherein said compositions are characterized also by an infrared spectrum of the type shown in FIG. 2.

5. The process of claim 4, wherein said infrared spectrum comprises also a band at 750 cm⁻¹.

6. The process according to claim 1, wherein said compositions contain a titanium amount (expressed as $TiO_2$) from 1 to 50%, preferably from 4.5 to 50% by weight.

7. The process according to claim 1, wherein said compositions have a surface area from 10 to 800 (preferably from 200 to 800) m²/g, a volume of the pores from 0.1 to 2.5 cm³/g and an average pore diameter greater than 0.70 nm and preferably from 1 to 40 nm.

8. The process according to claim 1, wherein said compositions are obtained by using, as a titanium source, a compound selected from:
- alkyl-titaniates and in particular tetraisopropyltitanate and di-isopropyl bis(triethanolamine)-titanate;
- titanium halides and in particular titanium tetrachloride ($TiCl_4$) and titanium trichloride ($TiCl_3$);
- complex titanates and in particular ammonium hexafluorotitaniate $(NH_4)_2TiF_6$;
- combinations and equivalents thereof.

9. The process according to claim 1, wherein said compositions are obtained by using, as a titanium source, a compound selected from $TiCl_4$; $(NH_4)_2TiF_6$; tetraisopropyl-titanate; di-isopropyl-bis(triethanolamine)-titanate.

10. The process according to claim 1, wherein the oxime is obtained by means of catalytic ammoximation of an aldehyde of formula $R_1CHO$, where $R_1$ is selected from the alkyl, cycloalkyl, aryl or heterocyclic groups having from 1 to 20 carbon atoms.

11. The process of claim 1, wherein the oxime is obtained by means of ammoximation of a ketone of formula $R_2-CO-R_3$, where $R_2$ and $R_3$, like or different from each other, have the same meaning as $R_1$ in claim 10 and can be linked, at their ends, to form a carbocyclic or heterocyclic ring.

12. The process of claim 1, wherein the oxime is obtained by ammoximation of a compound selected from acetone, cyclohexanone, methyl-ethyl-ketone, acetophenone, benzophenone, t.butyl-cyclohexanone, cyclo-dodecanone, enanthic aldehyde and benzaldehyde.

13. The process of claim 1, wherein the catalytic compositions are obtained by hydrolyzing alcoholic solutions of a silicon alcoholate and of a titanium alcoholate.

14. The process of claim 1, wherein the catalytic compositions are obtained from aqueous solutions of water-soluble silicon compounds and of water-soluble titanium compounds, by means of co-precipitation with a base and in particular with ammonium hydroxide ($NH_4OH$).

15. The process of claim 1, wherein the catalytic compositions are obtained by impregnating an amorphous silica with an aqueous solution of a water-soluble titanium compound.

16. The process of claim 1, wherein the catalytic compositions are obtained by causing a titanium volatile compound, in the vapor form, to be absorbed by an amorphous silica.

17. The process of claim 1, wherein the catalytic compositions are prepared by impregnating an amorphous silica with the non-aqueous solution of a titanium compound which is soluble in the non-aqueous medium.

18. The process of claim 1, wherein the catalytic compositions are calcined, before being used, at a temperature from 50° to 800° C.

* * * * *